United States Patent [19]

Abbott et al.

[11] Patent Number: 4,524,135
[45] Date of Patent: Jun. 18, 1985

[54] A-21978C CYCLIC PEPTIDES

[75] Inventors: Bernard J. Abbott, Greenwood; Manuel Debono, Indianapolis; David S. Fukuda, Brownsburg, all of Ind.

[73] Assignee: Eli Lilly and Company, Indianapolis, Ind.

[21] Appl. No.: 637,666

[22] Filed: Aug. 3, 1984

Related U.S. Application Data

[60] Division of Ser. No. 575,648, Jan. 31, 1984, Pat. No. 4,482,487, which is a continuation of Ser. No. 493,446, Jun. 13, 1983, abandoned, which is a continuation-in-part of Ser. No. 380,497, May 21, 1982, abandoned.

[51] Int. Cl.³ .................. C12P 21/06; C12P 21/04; C12R 1/045
[52] U.S. Cl. ........................... 435/69; 435/71; 435/827
[58] Field of Search ................. 435/69, 71, 827

[56] References Cited

U.S. PATENT DOCUMENTS

| | | | |
|---|---|---|---|
| 3,150,059 | 9/1964 | Kleinschmidt et al. | 260/112.5 R |
| 4,050,989 | 9/1977 | Kuwana et al. | 260/112.5 R |
| 4,208,403 | 6/1980 | Hamill et al. | 424/115 |
| 4,293,482 | 10/1981 | Abbott et al. | 260/112.5 R |
| 4,293,490 | 10/1981 | Abbott et al. | 260/112.5 R |
| 4,299,762 | 11/1981 | Abbott et al. | 260/112.5 R |
| 4,299,763 | 11/1981 | Abbott et al. | 260/112.5 R |
| 4,304,716 | 12/1981 | Abbott et al. | 260/112.5 R |
| 4,322,406 | 3/1982 | Debono et al. | 424/118 |
| 4,482,487 | 11/1984 | Abbott et al. | 260/112.5 R |

FOREIGN PATENT DOCUMENTS 405867 7/1963 Japan ................... 260/112.5 R

OTHER PUBLICATIONS

T. Kato et al., *J. Antibiotics*, 29, (12), 1339–1340, (1976).
S. Chihara et al., *Agr. Biol. Chem.*, 37, (11), 2455–2463, (1973).
S. Chihara et al., ibid., 37, (12), 2709–2717, (1973).
S. Chihara et al., ibid., 38, (3), 521–529, (1974).
S. Chihara et al., ibid., 38, (10), 1767–1777, (1974).
T. Suzuki et al., *J. Biochem.*, 56, (4), 335–343, (1964).
J. M. Weber et al., *J. Antibiotics*, 31, (4), 373–374, (1978).
J. Shoji et al., ibid., 28, 764–769, (1975).
J. Shoji et al., ibid., 29, (4), 380–389, (1976).
J. Shoji et al., ibid., 29, (12), 1268–1274; 1275–1280, (1976).

*Primary Examiner*—Delbert R. Phillips
*Attorney, Agent, or Firm*—Nancy J. Harrison; Arthur R. Whale

[57] ABSTRACT

A-21978C cyclic peptides of the formula

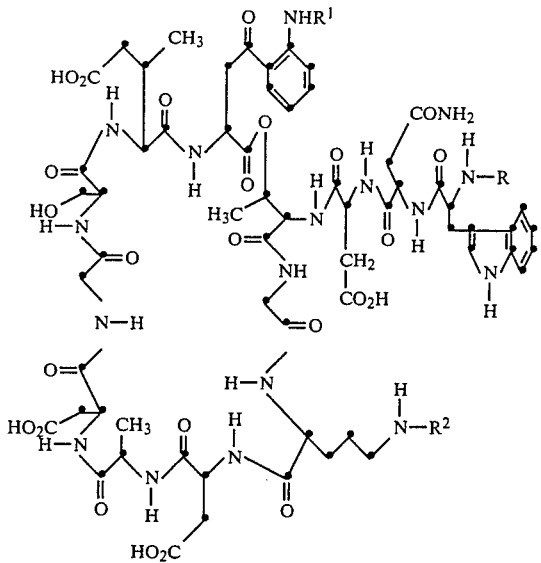

wherein R is selected from the group consisting of hydrogen, an amino-protecting group, 8-methyldecanoyl, 10-methylundecanoyl, 10-methyldodecanoyl, the specific $C_{10}$-alkanoyl group of A-21978C factor $C_0$ and the specific $C_{12}$-alkanoyl groups of A-21978C factors $C_4$ and $C_5$; $R^1$ and $R^2$ are, independently, hydrogen or an amino-protecting group, and salts thereof, are prepared by enzymatic deacylation of an antibiotic selected from A-21978C complex, A-21978C factors $C_0$, $C_1$, $C_2$, $C_3$, $C_4$ and $C_5$ and blocked A-21978C complex and factors $C_0$, $C_1$, $C_2$, $C_3$, $C_4$ and $C_5$, using an enzyme produced by the Actinoplanaceae, preferably by *Actinoplanes utahensis*. The A-21978C cyclic peptides and salts thereof are useful intermediates to prepare new semi-synthetic antibacterial agents.

23 Claims, 2 Drawing Figures

A-21978C CYCLIC PEPTIDES

CROSS REFERENCE TO RELATED APPLICATION

This application is a division of application Ser. No. 575,648, filed Jan. 31, 1984, now U.S. Pat. No. 4,482,487, which in turn is a continuation of application Ser. No. 493,446, filed June 13, 1983, now abandoned, which in turn is a continuation-in-part of application Ser. No. 380,497, filed May 21, 1982, now abandoned.

SUMMARY OF THE INVENTION

This invention relates to A-21978C cyclic peptides which have formula 1:

wherein R is selected from the group consisting of hydrogen, an amino-protecting group, 8-methyldecanoyl, 10-methylundecanoyl, 10-methyldodecanoyl, the specific $C_{10}$-alkanoyl group of A-21978C factor $C_0$ and the specific $C_{12}$-alkanoyl groups of A-21978C factors $C_4$ and $C_5$; $R^1$ and $R^2$ are, independently, hydrogen or an amino-protecting group; provided that, when R is other than hydrogen or an amino-protecting group, at least one of $R^1$ and $R^2$ must be an amino-protecting group; and the salts of these peptides. The A-21978C cyclic peptides and salts thereof are useful as intermediates in the preparation of semi-synthetic antibacterial agents.

The compounds of formula 1 wherein R is other than hydrogen or an amino-protecting group are blocked antibiotic A-21978C factors $C_0$, $C_1$, $C_2$, $C_3$, $C_4$ and $C_5$. These blocked antibiotic compounds are useful intermediates to certain peptides of formula 1, i.e. those wherein R is hydrogen and at least one of $R^1$ and $R^2$ is an amino-protecting group.

The compound of formula 1 wherein R, $R^1$ and $R^2$ each represent hydrogen is the common cyclic peptide present in antibiotic A-21978C factors $C_0$, $C_1$, $C_2$, $C_3$, $C_4$ and $C_5$. For convenience herein, this compound will be called A-21978C nucleus. This compound can also be represented by formula 2:

wherein 3MG represents L-threo-3-methylglutamic acid.

In another aspect, this invention relates to a method of enzymatically deacylating an antibiotic selected from A-21978C complex, A-21978C factors $C_0$, $C_1$, $C_2$, $C_3$, $C_4$, and $C_5$, blocked A-21978C complex, and blocked A-21978C factors $C_0$, $C_1$, $C_2$, $C_3$, $C_4$ and $C_5$. The naturally occurring A-21978C factors have a common cyclic peptide nucleus, but each has a different fatty acid group. The method of removing the fatty acid groups from the A-21978C factors and blocked factors provided by this invention comprises exposing the antibiotic or blocked antibiotic in an aqueous medium to an enzyme produced by a microorganism of the family Actinoplanaceae until substantial deacylation is accomplished.

A preferred method of this invention comprises using an enzyme produced by the microorganism *Actinoplanes utahensis* NRRL 12052 to cleave the fatty acid side chain. Deacylation is ordinarily accomplished by adding the appropriate antibiotic or blocked antibiotic to a culture of *A. utahensis* and permitting the culture to incubate until deacylation is accomplished. The A-21978C cyclic peptide or blocked peptide thereby obtained is separated from the fermentation broth by methods known in the art.

The A-21978C cyclic peptides of formula 1 are useful in that they can be reacylated to provide new antibiotic substances.

DESCRIPTION OF THE DRAWINGS

The following infrared absorption spectra, run in KBr disc, are presented in the accompanying drawings.

DETAILED DESCRIPTION OF THE INVENTION

In this specification the following abbreviations, most of which are commonly known in the art, are used:

Ala: alanine
Asp: aspartic acid
Gly: glycine
Kyn: kynurenine
Orn: ornithine
Ser: serine
Thr: threonine
Trp: tryptophan
t-BOC: tert-butoxycarbonyl
Cbz: benzyloxycarbonyl
DMF dimethylformamide
THF: tetrahydrofuran
HPLC: high-performance liquid chromatography
TLC: thin-layer chromatography
UV: ultraviolet

FIELD OF THE INVENTION

Although there are many known antibacterial agents, the need for improved antibiotics continues. Antibiotics differ in their effectiveness against pathogenic organisms, and resistant organism strains continually develop. In addition, individual patients often suffer serious reactions to specific antibiotics, due to hypersensitivity and/or to toxic effects. There is, therefore, a continuing need for new and improved antibiotics.

THE PRIOR ART The A-21978C antibiotics are closely related, acidic peptide antibiotics. Members of this class of antibiotics which were previously known include crystallomycin, amphomycin, zaomycin, aspartocin, and glumamycin [see T. Korzybski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., *J. Antibiotics* 21, 439–443 (1968)]; laspartomycin [H. Naganawa, et al., *J. Antibiotics* 21, 55–62 (1968)]; brevistin [J. Shoji and T. Kato, *J. Antibiotics* 29, 380–389 (1976)]; cerexin A [J. Shoji, et al., *J. Antibiotics* 29, 1268–1274 (1976)] and cerexin B [J. Shoji and T. Kato, *J. Antibiotics* 29, 1275–1280 (1976)]. Of these antibiotics, brevistin, cerexin A and cerexin B appear to be most closely related to the A-21978C antibiotics.

The A-21978C antibiotics are described by Robert L. Hamill and Marvin M. Hoehn in U.S. Pat. No. 4,208,403, issued June 17, 1980, which is incorporated herein by reference. As described in U.S. Pat. No. 4,208,403, the A-21978 antibiotic complex contains a major component, factor C, which is itself a complex of closely related factors. A-21978 factor C, which is called the A-21978C complex, contains individual factors $C_0$, $C_1$, $C_2$, $C_3$, $C_4$ and $C_5$. Factors $C_1$, $C_2$ and $C_3$ are major factors; and factors $C_0$, $C_4$ and $C_5$ are minor factors. The structure of the A-21978C factors is shown in formula 3:

wherein 3MG represents L-threo-3-methylglutamic acid, and $R^N$ represents a specific fatty acid moiety. The specific $R^N$ groups of the factors are as follows:

| A-21978C Factor | $R^N$ Moiety |
| --- | --- |
| $C_1$ | 8-methyldecanoyl |
| $C_2$ | 10-methylundecanoyl |
| $C_3$ | 10-methyldodecanoyl |
| $C_0$ | $C_{10}$-alkanoyl* |
| $C_4$ | $C_{12}$-alkanoyl* |
| $C_5$ | $C_{12}$-alkanoyl* |

*Identity not yet determined

Kleinschmidt et al. in U.S. Pat. No. 3,150,059, issued in 1964, described an enzyme elaborated by the Actinoplanaceae which was capable of deacylating penicillin antibiotics. Abbott and Fukuda in U.S. Pat. Nos. 4,293,482, 4,299,764, 4,299,762, 4,304,716, and 4,293,490, all issued in 1981, reported that an Actinoplanaceae enzyme was capable of deacylating the A-30912 type of cyclic peptide antibiotic. Reacylation of the A-30912 nucleus to form useful antifungal compounds was reported by Abbott and Fukuda in U.S. Pat. No. 4,287,120, issued in 1981, and in U.S. Pat. Nos. 4,320,052, 4,320,053, 4,320,054 and 4,322,338, issued in 1982; and by Debono in the following U.S. Pat. Nos. issued in 1981: 4,293,483, 4,293,488, 4,293,487, 4,293,485, 4,293,491, 4,293,489, 4,297,277, 4,289,692, 4,293,486 and 4,293,484.

In 1967 Kimura and Tatsuki, in Japanese Pat. No. 4058/67 (Derwent Abstr. 26695), described the enzymatic deacylation of the peptide antibiotic glumamycin. The microorganism catalyzing the deacylation was identified as closely related to *Pseudomonas dacunhae*. They stated that "deacylated derivatives of the compounds are useful as the material for synthesis of the related compounds, as in the case of 6-aminopenicillanic acid for penicillin", but gave no examples of re-acylation.

In 1965, Kimura and coworkers reported that a bacterium isolated from soil catalyzed the deacylation of the peptide antibiotic colistin (polymyxin E) (see Kimura, et al., Abstracts of Papers, 21st Meeting of the Pharmaceutical Society of Japan, Tokushima, October, 1965, p. 422). They reported that new derivatives of colistin were prepared by acylation of the deacylated nucleus, but did not discuss whether these derivatives had any activity.

Kato and Shoji [J. Antibiotics 29 (12), 1339–1340 (1976)] attempted to use the enzyme described by Kimura et al. to deacylate the cyclic peptide antibiotic octapeptin $C_1$. The enzyme did not catalyze the desired reaction. It was subsequently found that deacylation could be accomplished chemically by oxidation of the $\beta$-hydroxyl group of the fatty acid followed by treatment with hydroxylamine.

In 1973 Chihara and coworkers reported their work with colistin. In this work two plant proteases, ficin and papain, were used to hydrolyze colistin to a nonapeptide and a fatty acyl $\alpha,\gamma$-diaminobutyric acid residue. The plant enzymes, however, in addition to removing the fatty acid acyl substituent, also removed the terminal amino acid of the colistin molecule [see S. Chihara et al., Agr. Biol. Chem. 37 (11), 2455–2463 (1973); ibid. 37 (12), 2709–2717 (1973); ibid. 38 (3), 521–529 (1974); and ibid. 38 (10), 1767–1777 (1974)]. The colistin nonapeptide was isolated and then reacylated with a variety of fatty acid chlorides. Subsequently, Chihara's group produced N-fatty acyl mono-acyl derivatives of colistin nonapeptide. These derivatives restored a tenth amino acid to the colistin nonapeptide and were used to study structure-activity relationships.

The polymyxin antibiotics have been hydrolyzed with the enzyme subtilopeptidase A [see T. Suzuki et al., J. Biochem. 56 (4), 335–343 (1964)]. This enzyme deacylated the peptides, but in addition hydrolyzed some of the peptide bonds so that a variety of peptide products resulted.

In 1978 Weber and Perlman reported that a Corynebacterium isolated from soil inactivated the peptide antibiotic amphomycin by deacylation of the isotridecanoic acid side chain [see J. Antibiotics 31 (4), 373–374 (1978)].

Kuwana et al. in U.S. Pat. No. 4,050,989, issued in 1977, described the deacylation of pepsin-inhibiting peptides (pepsidines) by an enzyme from Bacillus pumilus and the use of these products to prepare N-acyl-pentapeptide homologs.

Shoji and coworkers deacylated the cyclic peptide antibiotics cerexin A, cerexin B, and brevistin in order to determine the structures of these antibiotics [see J. Shoji and T. Kato, J. Antibiotics 28, 764–769 (1975) and ibid. 29 (4), 380–389 (1976); and J. Shoji et al., ibid. 29 (12), 1268–1274 (1976); and ibid. 29 (12), 1275–1280 (1976)]. Deacylation was accomplished with an enzyme preparation prepared from Pseudomonas sp. M-6-3 (polymyxin acylase) and by chemical means. Chemical deacylation, however, resulted in extensive side reactions.

Despite the contributions of these groups, it is extremely difficult, when confronted with the problem of deacylating a peptide antibiotic having a different structure, to know whether an enzyme exists which can be used for this purpose. Finding such an enzyme is even more difficult when the substrate antibiotic contains a cyclic peptide nucleus. Enzymes have a high degree of specificity. Differences in the peptide moiety and in the side chain of the substrate antibiotic will affect the outcome of the deacylation attempt. In addition, many microorganisms make a large number of peptidases which attack different portions of the peptide moiety. This frequently leads to intractable mixtures of products.

Thus, it was most surprising that what may be the same enzyme which was used to deacylate penicillins and the A-30912 antibiotics could also be used successfully to deacylate the A-21978C antibiotics. In each of the A-21978C antibiotics (formula 3), the fatty acid side chain ($R^N$) is attached at the $\alpha$-amino group of the tryptophan residue. We have discovered that the fatty acid side chain can be cleaved by an enzyme without affecting the chemical integrity of the remainder of the A-21978C peptide.

The present invention relates also to novel A-21978C cyclic peptides having formula 1 wherein R is selected from the group consisting of hydrogen, an amino-protecting group, 8-methyldecanoyl, 10-methylundecanoyl, 10-methyldodecanoyl, the specific $C_{10}$-alkanoyl group of A-21978C factor $C_0$ and the specific $C_{12}$-alkanoyl moieties of A-21978C factors $C_4$ and $C_5$; $R^1$ and $R^2$ are, independently, hydrogen or an amino-protecting group; provided that, when R is other than hydrogen or an amino-protecting group, at least one of $R^1$ and $R^2$ must be an amino-protecting group; and to the salts of these compounds. The cyclic peptides of formula 1 and their salts are useful intermediates in the preparation of new semi-synthetic antibacterial agents which are especially useful against gram-positive microorganisms.

The term "amino-protecting group" refers to a recognized amino-protecting group which is compatible with the other functional groups in the A-21978C molecule. Preferably, amino-protecting groups are those which can be readily removed subsequently. Examples of suitable protecting groups can be found in "Protective Groups in Organic Synthesis" by Theodora W. Greene, John Wiley and Sons, N.Y. 1981, Chapter 7. Especially preferable amino-protecting groups are the tert-butoxycarbonyl and benzyloxycarbonyl groups.

The cyclic peptides of formula 1 wherein R is hydrogen include the common cyclic peptide of A-21978C factors $C_0$, $C_1$, $C_2$, $C_3$, $C_4$ and $C_5$ (A-21978C nucleus) and blocked derivatives of A-21978C nucleus. A-21978C nucleus, i.e. the compound of formula 1 wherein each of R, $R^1$ and $R^2$ represents hydrogen, is alternately described by formula 2.

A-21978C nucleus has the following characteristics:

Form: white amorphous solid which fluoresces under short-wave UV.

Empirical formula: $C_{62}H_{83}N_{17}O_{25}$.

Molecular weight: 1465.

Solubility: soluble in water.

Figure 1:
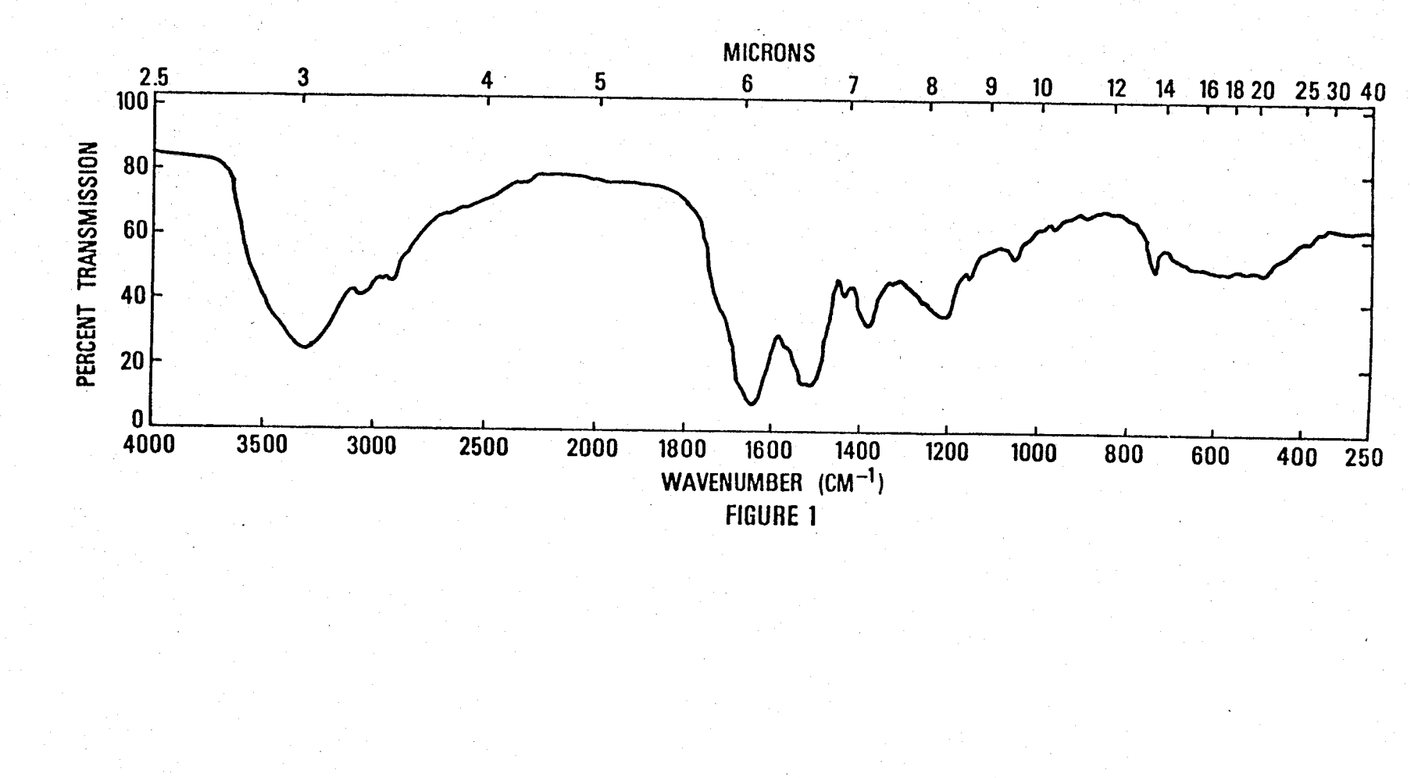
FIG. 1—A-21978C nucleus (formula 1, R, $R^1$, $R^2$=H)

Infrared absorption spectrum (KBr disc): shown in FIG. 1 of the accompanying drawings; absorption maxima are observed at the following frequencies ($cm^{-1}$):

3300 (broad), 3042 (weak), 2909 (weak), 1655 (strong), 1530 (strong), 1451 (weak), 1399 (medium), 1222 (medium), 1165 (weak), 1063 (weak) and 758 (medium to weak).

Ultraviolet (UV) absorption spectrum (methanol): UV maxima 223 nm ($\epsilon$41,482) and 260 nm ($\epsilon$8,687).

Electrometric titration (66% aqueous dimethylformamide): indicates the presence of four titratable groups with $pK_a$ values of about 5.2, 6.7, 8.5 and 11.1 (initial pH 6.12).

A particularly useful cyclic peptide of formula 1 is the compound wherein R and $R^1$ represent hydrogen and $R^2$ represents tert-butoxycarbonyl. This compound is designated "t-BOC nucleus" for convenience herein. A-21978C t-BOC nucleus has the following characteristics:

Form: white amorphous solid which fluoresces under short-wave UV.

Empirical formula: $C_{67}H_{91}N_{17}O_{27}$.

Molecular weight: 1565.

Solubility: soluble in water.

Figure 2:
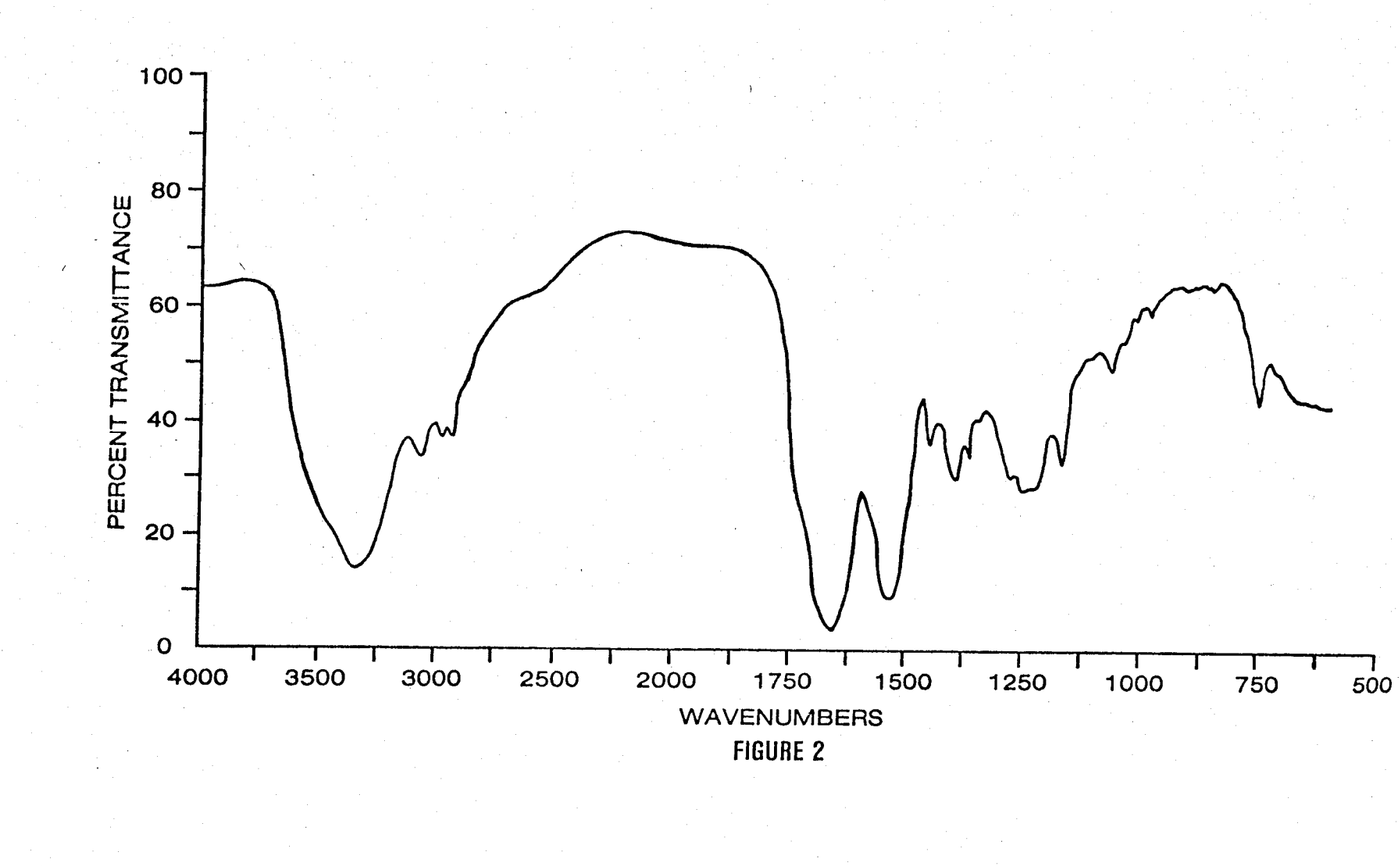
FIG. 2—A-21978C $N_{Orn}$-t-BOC nucleus (formula 1, R and $R^1$=H; $R^2$=tert-butyloxycarbonyl)

Infrared absorption spectrum (KBr disc): shown in FIG. 2 of the accompanying drawings; absorption maxima are observed at the following frequencies ($cm^{-1}$):

3345 (broad), 3065 (weak), 2975 (weak), 2936 (weak), ~1710 (shoulder), 1660 (strong), 1530 (strong), 1452 (weak), 1395 (medium), 1368 (weak), 1341 (weak), 1250 (medium), 1228 (medium), 1166 (medium to weak) and 1063 (weak).

Ultraviolet absorption spectrum (90% ethanol): UV maxima 220 nm ($\epsilon$42,000) and 260 nm ($\epsilon$10,600).

High-performance liquid chromatography: retention time=6 min on 4.6-$\times$300-mm silica-gel $C_{18}$ column, using $H_2O/CH_3CN/CH_3OH$ (80:15:5) solvent containing 0.2% $NH_4OAc$ at a flow rate of 2 ml/min with UV detection.

The blocked A-21978C factors of this invention are those compounds of formula 1 wherein at least one of $R^1$ and $R^2$ is an amino-protecting group and R is selected from 8-methyldecanoyl, 10-methylundecanoyl, 10-methyldodecanoyl, the specific $C_{10}$-alkanoyl group of A-21978C factor $C_0$ and the specific $C_{12}$-alkanoyl groups of A-21978C factors $C_4$ and $C_5$.

The A-21978C blocked factors and cyclic peptides of this invention are capable of forming salts. These salts are also part of this invention. Such salts are useful, for example, for separating and purifying the compounds. Pharmaceutically-acceptable alkali-metal, alkaline-earth-metal, amine and acid-addition salts are particularly useful.

For example, the A-21978C cyclic peptides of formula 1 have four free carboxyl groups which can form salts. Partial, mixed and complete salts of these carboxyl groups are, therefore, contemplated as part of this invention. In preparing these salts, pH levels greater than 10 should be avoided due to the instability of the compounds at such levels.

Representative and suitable alkali-metal and alkaline-earth metal salts of the A-21978C cyclic peptides of formula 1 include the sodium, potassium, lithium, cesium, rubidium, barium, calcium and magnesium salts. Suitable amine salts of the A-21978C cyclic peptides include the ammonium and the primary, secondary, and tertiary $C_1-C_4$-alkylammonium and hydroxy $C_2-C_4$-alkylammonium salts. Illustrative amine salts include those formed by reaction of an A-21978C cyclic peptide with ammonium hydroxide, methylamine, sec-butylamine, isopropylamine, diethyulamine, di-isopropylamine, ethanolamine, triethylamine, 3-amino-1-propanol, and the like.

The alkali-metal and alkaline-earth-metal cationic salts of the A-21978C cyclic peptides of formula 1 are prepared according to procedures commonly used for the preparation of cationic salts. For example, the free acid form of the A-21978C cyclic peptide is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of an A-21978C cyclic peptide in a suitable solvent such as acetone; the solvent and excess amine can be removed by evaporation.

The A-21978C cyclic peptides of this invention also have free amino groups and can, therefore, form acid addition salts. Such salts are also part of this invention. Representative and suitable acid-addition salts of the A-21978C cyclic peptides include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic, and like acids.

Preparation of the A-21978C Cyclic Peptides

The A-21978C cyclic peptides of formula 1 wheren R is hydrogen are obtained by deacylating a peptide antibiotic selected from the group consisting of A-21978C factors $C_0$, $C_1$, $C_2$, $C_3$, $C_4$ and $C_5$ and blocked A-21978C factors $C_0$, $C_1$, $C_2$, $C_3$, $C_4$ and $C_5$.

I. Preparation of the Substrates

A-21978C factors $C_0$, $C_1$, $C_2$, $C_3$, $C_4$ and $C_5$ are prepared as described in U.S. Pat. No. 4,208,403. These factors are components of the A-21978C complex which is part of the A-21978 complex.

The A-21978 complex is produced by culturing *Streptomyces roseosporus* NRRL 11379 under submerged aerobic fermentation conditions until a substantial level of antibiotic activity is produced. The A-21978 complex is separated by filtering the fermentation broth, lowering the pH of the filtrate to about pH 3, allowing the complex to precipitate, and separating the complex by filtration. The separated complex may be further purified by extraction techniques. For isolation of the individual A-21978C complex and factors, chromatographic separations are required.

Blocked A-21978C complex and the blocked A-21978C factors $C_0$, $C_1$, $C_2$, $C_3$, $C_4$ and $C_5$ of this invention (compounds of formula 1 wherein R is selected from the group consisting of 8-methyldecanoyl, 10-methylundecanoyl, 10-methydodecanoyl, and the $C_{10}$- and $C_{12}$-alkanoyl groups of factors $C_0$, $C_4$ and $C_5$) are prepared using standard procedures for protecting amino groups in peptides. The protecting groups are selected from the various known amino-protecting groups such as, for example, benzyloxycarbonyl, t-butoxycarbonyl, t-amyloxycarbonyl, isobornyloxycarbonyl, adamantyloxyt-amyloxycarbonyl, o-nitrophenylthio, diphenylphosphinothioyl, chloro- or nitrobenzyloxycarbonyl, or the like.

Blocked A-21978C complex is especially advantageous as a substrate. It is prepared from the A-21978C complex, thereby avoiding the separation steps required to obtain the individual A-21978C factors; but, when it is deacylated, it gives a single product, i.e. the appropriately blocked nucleus.

II. The Deacylation Procedure

A. Preparation of the Enzyme

1. The Producing Microorganism

The enzyme which is useful for deacylation of A-21978C factors $C_0$, $C_1$, $C_2$, $C_3$, $C_4$ and $C_5$ and blocked factors $C_0$, $C_1$, $C_2$, $C_3$, $C_4$ and $C_5$ is produced by certain microorganisms of the family Actinoplanaceae, preferably the microorganism *Actinoplanes utahensis* NRRL 12052.

The enzyme may be the same enzyme which has been used to deacylate penicillins (see Walter J. Kleinschmidt, Walter E. Wright, Frederick W. Kavanagh, and William M. Stark in U.S. Pat. No. 3,150,059, issued Sept. 22, 1964) and/or the same enzyme used to deacylate the A-30912-type antibiotics (see Bernard J. Abbott and David S. Fukuda in U.S. Pat. Nos. 4,293,482, 4,293,490, 4,299,762, 4,299,763 and 4,304,716). Although a preferred method of cultivating *A. utahensis* NRRL 12052 to produce this enzyme is described in Example 1, it will be recognized by those skilled in the art that other methods may be used.

The Actinoplanaceae are a family of micro-organisms of the order Actinomycetales. First described by Dr. John N. Couch, this family was established in 1955 [*J. Elisha Mitchell Sci. Soc.* 71, 148–155 (1955)]. The characteristics of the family and of many individual genera are found in "Bergey's Manual of Determinative Bacteriology", 8th ed., R. E. Buchanan and N. E. Gibbons, Eds., The Williams & Wilkins Co., Baltimore, Md., 1974, pages 706–723. Ten genera have thus far been distinguished: I. Actinoplanes (the type genus and thus far the most common genus); II. Spirillospora; III. Streptosporangium; IV. Amorphosporangium; V. Ampullariella; VI. Pilimelia; VII. Planomonospora; VIII. Planobispora; IX. Dactylosporangium; and X. Kitasatoa.

Some of the species and varieties which have been isolated and characterized so far are: *Actinoplanes hilippinensis, Actinoplanes armeniacus, Actinoplanes utahensis,* and *Actinoplanes missouriensis; Spirillospora albida; Streptosporiangium roseum, Streptosporangium vulgare, Streptosporangium roseum* var. *hollandensis, Streptosporangium album, Streptosporangium viridialbum, Amorphosporangium auranticolor, Ampullariella regularis, Ampullariella campanulata, Ampullariella lobata, Ampullariella digitata, Pilimelia terevasa, Pilimelia anulata, Planomonospora parontospora, Planomonospora venezuelensis, Planobispora longispora, Planobispora rosea, Dactylosporangium aurantiacum,* and *Dactylosporangium thailandense.*

The genus Actinoplanes is a preferred source of the enzyme which is useful for this invention. Within the genus Actinoplanes, the species *Actinoplanes utahensis* is an especially preferred source.

Cultures of representative useful species are available to the public from the Northern Regional Research Center, Agricultural Research Culture Collection (NRRL), U.S. Department of Agriculture, 1815 North University St., Peoria, Ill. 61604, U.S.A., under the following accession numbers:

| | |
|---|---|
| *Actinoplanes utahensis* | NRRL 12052 |
| *Actinoplanes missouriensis* | NRRL 12053 |
| Actinoplanes sp. | NRRL 8122 |
| Actinoplanes sp. | NRRL 12065 |
| *Streptosporangium roseum* var. *hollandensis* | NRRL 12064 |

*A. utahensis* NRRL 12052 was derived from a parent culture which was also deposited with the American Type Culture Collection (ATCC), 12301 Parklawn Drive, Rockville, Md. 20852 (*A. utahensis* ATCC 14539). The *A. utahensis* ATCC 14539 culture may also be used as a source of the enzyme.

*A. missouriensis* NRRL 12053 was derived from a culture which was also deposited with ATCC (*A. missouriensis* ATCC 14538) and which is another source of the enzyme.

The effectiveness of any given strain of microorganism within the family Actinoplanaceae for carrying out the deacylation of this invention is determined by the following procedure. A suitable growth medium is inoculated with the microorganism. The culture is incubated at about 30° C. for two or three days on a rotary shaker. One of the substrate antibiotics is then added to the culture. The pH of the fermentation medium is maintained at about pH 7.0. The culture is monitored for activity using a *Micrococcus luteus* assay. This procedure is described in Sect. D. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. lauroyl, n-decanoyl or n-dodecanoyl) to restore activity. Reduction in antibiotic activity is difficult to distinguish when deacylating blocked A-21978C material because addition of the blocking group causes an 80–90% reduction in antibiotic activity.

2. Conditions for Enzyme Production

Production of the enzyme occurs under conditions satisfactory for growth of the Actinoplanaceae, i.e., a temperature between about 25° and about 30° C. and a pH of between about 5.0 and about 8.0, with agitation and aeration. The culture medium should contain (a) an assimilable carbon source such as sucrose, glucose, glycerol, or the like; (b) a nitrogen source such as peptone, urea, ammonium sulfate, or the like; (c) a phosphate source such as a soluble phosphate salt; and (d) inorganic salts found generally to be effective in promoting the growth of microorganisms. An effective amount of the enzyme is generally obtained in from about 40 to about 60 hours after the beginning of the growth cycle and persists for some time after the effective growth has been reached. The amount of enzyme produced varies from species to species of the organism and in response to different growth conditions.

As will be apparent to those in the field, the microorganisms, such as *Actinoplanes utahensis* NRRL 12052, which produce the enzyme are subject to variation. For example, artificial variants and mutants of these strains may be obtained by treatment with various known mutagens such as ultraviolet rays, X-rays, high-frequency waves, radioactive rays, and chemicals. All natural and artificial variants and mutants which are obtained from the Actinoplanaceae and which produce the enzyme may be used in this invention.

B. Deacylation Conditions

The substrate used as the starting material is preferably added to the culture of Actinoplanaceae after the culture has been incubated for about 48 hours. The concentration of substrate in the conversion medium can vary widely. For maximum use of the enzyme and for substantially complete deacylation within a three-hour period, however, the concentration of substrate will generally range from about one to about three mg/ml. Lower concentrations can be used, but may not make maximum use of the enzyme; higher concentrations can also be used, but the substrate may not be completely deacylated unless the fermentation time is extended.

Conversion of the substrate antibiotic to A-21978C nucleus according to this invention proceeds best when the pH of the fermentation medium is maintained in the range of from about 7.0 to about 7.2. Below pH 7, deacylation proceeds slowly; as pH values move above pH 7.2, the nucleus which is formed is increasingly subject to alkaline hydrolysis. In stirred fermentors the pH may be controlled by sensor controllers. Where this is impractical, such as in flask fermentors, pH may be controlled by adding 0.1 molar phosphate buffer to the medium prior to addition of the substrate.

After addition of the substrate, incubation of the culture should be continued for about 3–6 hours or longer. The purity of the substrate will affect the rate of deacylation. For example, a substrate having a purity of greater than 50 percent is deacylated at a rate of about 2.5 mg/ml of antibiotic in 3 hours. When substrates of lower purity are used, the deacylation proceeds at a somewhat slower rate.

Multiple substrate feedings may be made. For example, 0.75 mg/ml of antibiotic may be fed at 24-hour intervals for at least five or more additions.

The deacylation can be carried out over a broad temperature range, e.g. from about 20° to about 45° C. It is preferable, however, to carry out the deacylation at a temperature of about 30° C. for optimum deacylation and stability of substrate and nucleus.

C. The Substrate

It is preferable, but not essential, to use purified antibiotic as the substrate. Because purified substrate is soluble in water or in buffer, it can be handled more conveniently. Moreover, with purified substrate the deacylation proceeds more rapidly. Semipurified substrates containing as little as 15 percent of the starting antibiotic have been deacylated successfully.

The substrate antibiotics have antibacterial activity. Thus, while the substrate materials (especially those of low purity) may harbor bacterial cells or spores which presumably could grow in the deacylation medium and affect the deacylation reaction or the stability of the starting antibiotic or the product nucleus, this has not been observed. It is not necessary, therefore, that the substrates be sterile, especially for short deacylation periods.

D. Monitoring the Deacylation

A-21978C factors $C_0$, $C_1$, $C_2$, $C_3$, $C_4$ and $C_5$ are antibacterial agents which are especially active against *Micrococcus luteus*. For this reason an assay using *M. luteus* is preferable for determining quantities of substrate present. The A-21978C nucleus which is formed is water soluble, but is biologically inactive. Reduction in biological activity is, therefore, a quick, presumptive test for deacylation.

The amount of nucleus formed can be quantitated by HPLC analysis, using the system herein described.

E. Use of Resting Cells

An alternate method of deacylation involves removing the Actinoplanaceae cells from the culture medium, resuspending the cells in a buffer solution, and carrying out the deacylation as described in Sect. B. When this method is used, the enzymatically active mycelia can be reused. For example, *A. utahensis* NRRL 12052 mycelia retain deacylase activity after storage for one month or longer under refrigeration (4°–8° C.) or in the frozen state ($-20°$ C.). A preferred buffer solution is 0.1 molar phosphate buffer.

F. Immobilized Enzymes

Yet another method of carrying out the deacylation is to immobilize the enzyme by methods known in the art. (See, for example, "Biomedical Applications of Immobilized Enzymes and Proteins", Thomas Ming Swi Chang, Ed., Plenum Press, N.Y., 1977; Vol. 1.) The immobilized enzyme can then be used in a column (or other suitable type of reactor) to effect the deacylation.

In addition, the microorganism itself can be immobilized and used to catalyze the deacylation reaction.

Utility of the A-21978C Cyclic Peptides

The A-21978C cyclic peptides and their salts are useful intermediates in the preparation of semi-synthetic antibacterial compounds. Useful antibacterial compounds prepared from the A-21978C cyclic peptides are described in our copending application (Bernard J. Abbott, Manuel Debono and David S. Fukuda, Ser. No. 382,012, filed May 21, 1982) and in two copending applications of Manuel Debono (Ser. Nos. 380,498 and 380,499), all of which are entitled DERIVATIVES OF A-21978C and which were filed May 21, 1982.

The Abbott, Debono and Fukuda Derivatives

The compounds described in the Abbott, Debono and Fukuda application have the general formula shown in formula 4:

in which R, R¹ and R² are, independently, hydrogen, C$_4$–C$_{14}$-alkyl, optionally substituted C$_2$–C$_{19}$-alkanoyl, C$_5$–C$_{19}$-alkenoyl or an amino-protecting group; R³, R⁴ and R⁵ are hydrogen or (i) R³ and R¹ and/or (ii) R⁴ and R and/or (iii) R⁵ and R², taken together, represent a C$_4$–C$_{14}$ alkylidene group; provided that (1) at least one of R, R¹ or R² must be other than hydrogen or an amino-protecting group, (2) at least one of R¹ or R² must be hydrogen or an amino-protecting group, (3) the R, R¹ and R² groups must together contain at least four carbon atoms and (4) when R¹ and R² are both selected from hydrogen or an amino-protecting group, R cannot be 8-methyldecanoyl, 10-methyldodecanoyl, 10-methylundecanoyl, the specific C$_{10}$-alkanoyl group of A-21978C$_0$ or the specific C$_{12}$-alkanoyl groups of A-21978C factors C$_4$ and C$_5$; and the salts thereof.

The term "C$_4$–C$_{14}$-alkylidenyl" refers to a group of the formula wherein R³ and R⁴ are hydrogen or an alkyl group of from 3 to 13 carbon atoms, provided that one of R³ and R⁴ must be other than hydrogen and further provided that the sum of the carbon atoms in R³ and R⁴ must be no greater than 13. Those compounds wherein one of R and R⁴, R¹ and R³ or R² and R⁵ represent C$_4$–C$_{14}$-alkylidenyl are known as Schiff's bases.

The term "C$_4$–C$_{14}$-alkyl" refers to a univalent saturated, straight- or branched-chain alkyl group containing from 4 to 14 carbon atoms. Those compounds wherein one of R, R¹ or R² are C$_4$–C$_{14}$-alkyl are prepared by reduction of the corresponding compounds where the R and R⁴, R¹ and R³ or R² and R⁵ group is C$_4$–C$_{14}$-alkylidenyl and are referred to herein as "reduced Schiff's bases".

The terms "optionally substituted C$_2$–C$_{19}$-alkanoyl" and "C$_5$–C$_{19}$-alkenoyl" refer to acyl groups derived from carboxylic acids containing from 2 to 19 and 5 to 19 carbon atoms, respectively. When the R group is alkanoyl, the alkyl portion is a univalent saturated, straight-chain or branched-chain hydrocarbon radical which can optionally bear one hydroxyl group or from one to three halo substituents selected from chlorine, bromide, and fluorine. When R is alkenoyl, the alkenyl portion is a univalent, unsaturated, straight-chain or branched-chain hydrocarbon radical containing not more than three double bonds. The double bond portion(s) of the unsaturated hydrocarbon chain may be either in the cis or trans configuration.

The term "amino-protecting group" refers to a recognized amino-protecting group as defined supra.

The following are preferred embodiments of the compounds of formula 4:

(a) The compounds wherein R is alkanoyl of the formula wherein n is an integer from 3 to 17;

(b) The compounds wherein R is alkanoyl of the formula wherein n is 5, 6, 7, 8, 9, 10, 11, 12, 13, or 14;

(c) The compounds wherein R is alkanoyl of the formula wherein n and m are each, independently, an integer from 0 to 14, provided that n+m must be no less than 1 and no greater than 15; and further provided that, when n is 0, m cannot be 8 and, when n is 1, m cannot be 6 or 8;

(d) The compounds wherein R is cis or trans alkenyl of the formula wherein n and m are each, independently, an integer from 0 to 14, provided that n+m must be no less than 1 and no greater than 15;

(e) The compounds wherein R is cis or trans alkenyl of the formula wherein n is an integer of from 4 to 15;

(f) The compounds wherein R is alkyl of the formula CH$_3$(CH$_2$)$_n$— and n is an integer from 5 to 12; and

(g) The compounds wherein R is:

15

-continued

The Debono Derivatives

The compounds described in the two Debono applications have the general formula 5:

16

A. The Debono Group I Derivatives

The derivatives of structure 5 described in Debono application Ser. No. 380,499 (Debono Group I) are those wherein R is hydrogen, 8-methyldecanoyl, 10-methyldodecanoyl, 10-methylundecanoyl, the specific $C_{10}$-alkanoyl group of A-21978$C_0$ or the specific $C_{12}$-alkanoyl groups of A-21978C factors $C_4$ and $C_5$, an amino-protecting group, an aminoacyl group of the formula wherein Q is $C_1$-$C_{16}$ alkylene or an N-alkanoylaminoacyl group of the formula wherein: W is a divalent aminoacyl radical of the formula:

wherein A is $C_1$-$C_{10}$ alkylene or $C_5$-$C_6$ cycloalkylene;

wherein $R^3$ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkoxy, $C_1$-$C_3$ alkylthio, carbamyl, or $C_1$-$C_3$ alkylcarbamyl;

wherein X is hydrogen chloro, bromo, iodo, amino, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

wherein $X^1$ is chloro, bromo, iodo, amino, hydroxy, $C_1$-$C_3$-alkyl or $C_1$-$C_3$-alkoxy;

(e) or (f)

wherein B is a divalent radical of the formula: —(CH$_2$)$_n$— and n is an integer from 1 to 3; —CH=CH—; —CH=CH—CH$_2$—; or R$^2$ is C$_1$–C$_{17}$ alkyl or C$_2$–C$_{17}$ alkenyl; and R$^1$ is hydrogen, an amino-protecting group, an aminoacyl group of the formula as herein defined, or an N-alkanoylaminoacyl group of the formula as herein defined; provided that, when R is other than aminoacyl or N-alkanoylaminoacyl, R$^1$ must be aminoacyl or N-alkanoylaminoacyl; and, when R$^1$ is an amino-protecting group, R must be aminoacyl or N-alkanoylaminoacyl; and the salts thereof.

The terms "alkylene", "alkyl", "alkoxy", "alkylthio", and "alkenyl" comprehend both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative C$_1$–C$_{10}$ or C$_1$–C$_{16}$ alkylene radicals which are preferred are:

in which R$^5$ is C$_1$–C$_4$ alkyl (i.e., methyl, ethyl, n-propyl, i-propyl, n-butyl, t-butyl, i-butyl, or 1-methylpropyl); —(CH$_2$)$_m$— in which m is an integer from 2 to 10; and CH$_3$—(CH$_2$)$_q$—CH—(CH$_2$)$_p$—, in which p is an integer from 1 to 8 and q is an integer from 0 to 7, provided that p+q must be no greater than 8.

Illustrative C$_1$–C$_{17}$ alkyl groups which are preferred are:

(a) CH$_3$—;

(b) —(CH$_2$)$_n$CH$_3$ wherein n is an integer from 1 to 16; and wherein r and s are, independently, an integer from 0 to 14 provided that r+s can be no greater than 14.

Illustrative C$_2$–C$_{17}$ alkenyl radicals which are preferred are:

(a) —(CH$_2$)$_t$—CH=CH—(CH$_2$)$_u$—CH$_3$ wherein t and u are, independently, an integer from 0 to 14 provided that t+u can be no greater than 14.

(b) —(CH$_2$)$_v$—CH=CH—(CH$_2$)$_y$—CH=CH—(CH$_2$)$_z$—CH$_3$ wherein v and z are, independently, an integer from 0 to 11 and y is an integer from 1 to 11 provided that v+y+z can be no greater than 11.

In particular, the following embodiments of the C$_1$–C$_{17}$ alkyl groups are preferred:
CH$_3$—
CH$_3$(CH$_2$)$_5$—
CH$_3$(CH$_2$)$_6$—
CH$_3$(CH$_2$)$_8$—
CH$_3$(CH$_2$)$_{10}$—
CH$_3$(CH$_2$)$_{12}$—
CH$_3$(CH$_2$)$_{14}$—
CH$_3$(CH$_2$)$_{16}$—

In particular, the following embodiments of the C$_2$–C$_{17}$ alkenyl groups are preferred:
cis-CH$_3$(CH$_2$)$_5$CH=CH(CH$_2$)$_7$—
trans-CH$_3$(CH$_2$)$_5$CH=CH(CH$_2$)$_7$—
cis-CH$_3$(CH$_2$)$_{10}$CH=CH(CH$_2$)$_4$—
trans-CH$_3$(CH$_2$)$_{10}$CH=CH(CH$_2$)$_4$—
cis-CH$_3$(CH$_2$)$_7$CH=CH(CH$_2$)$_7$—
trans-CH$_3$(CH$_2$)$_7$CH=CH(CH$_2$)$_7$—
cis-CH$_3$(CH$_2$)$_5$CH=CH(CH$_2$)$_9$—
trans-CH$_3$(CH$_2$)$_5$CH=CH(CH$_2$)$_9$—
cis, cis-CH$_3$(CH$_2$)$_4$CH=CHCH$_2$CH=CH(CH$_2$)$_7$—
trans, trans-CH$_3$(CH$_2$)$_4$CH=CHCH$_2$CH=CH(CH$_2$)$_7$—
cis,cis,cis-CH$_3$CH$_2$CH=CHCH$_2$CH=CHCH$_2$CH=CH—(CH$_2$)$_7$—.

When "W" is a divalent radical of the formula it will be recognized by those skilled in the art that the function and the —NH— function may be oriented on the benzene ring in the ortho, meta, or para configuration relative to each other. The substituent represented by X may be substituted at any available position of the benzene ring. Preferred embodiments are those in which X is hydrogen and the are oriented in the para configuration.

The terms "substituted phenyl" and "substituted benzyl", as defined by $R^3$ in formula 5, contemplate substitution of a group at any of the available positions in the benzene ring—i.e. the substituent may be in the ortho, meta, or para configuration. The term "$C_1$-$C_3$ alkyl" as defined by $R^3$ or X in formula 5 includes the methyl, ethyl, n-propyl, or i-propyl groups.

B. The Debono Group II Derivatives

The derivatives of structure 5 described in Debono application Ser. No. 380,498 (Debono Group II) are those wherein R is a substituted benzoyl group of the formula wherein X is hydrogen, chloro, bromo, iodo, nitro, $C_1$-$C_3$ alkyl, hydroxy, $C_1$-$C_3$ alkoxy, or $C_1$-$C_3$ alkylthio; $R^1$ is hydrogen or an amino-protecting group; and $R^2$ is $C_8$-$C_{15}$ alkyl; and the salts thereof.

The substituted benzoyl group, the and the —$OR^2$ function may be oriented on the benzene ring in the ortho, meta, or para position relative to each other. The para orientation for these groups is preferred. The substituent represented by X may be substituted at any available position of the benzene ring not occupied by these two groups.

The term "alkyl" comprehends both straight and branched hydrocarbon chains.

Illustrative $C_8$-$C_{15}$ alkyl radicals which are preferred for $R^2$ are:

(a) —$(CH_2)_nCH_3$ wherein n is an integer from 7 to 14; and wherein r and s are, independently, an integer from 0 to 12, provided that r+s can be no greater than 12 or no less than 5.

Preparation of the Derivatives

The compounds of formulas 4 and 5 are prepared by acylating a compound of formula 1 with the appropriate acyl side chain using methods conventional in the art for forming an amide bond. The acylation is accomplished, in general, by reacting the selected formula compound with an activated derivative of the acid corresponding to the desired acyl side chain group.

The term "activated derivative" means a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride or aryloxyformic acid anhydride) or (c) an activated ester (e.g. a 2,4,5-trichlorophenyl ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of formulas 4 and 5 is by the active ester method. The 2,4,5-trichlorophenyl ester of the desired acid is a preferred acylating agent. In this method, an excess amount of the active ester is reacted with a formula 1 compound at room temperature in a non-reactive organic solvent such as DMF. The reaction time is not critical, although a time of about 6 to about 20 hours is preferred. At the conclusion of the reaction, the solvent is removed, and the residue is purified by a recognized method, such as by column chromatography. t-BOC groups can be removed by treatment with trifluoroacetic acid/anisole/triethylsilane or, preferably, trifluoroacetic acid/1,2-ethanedithiol for from about three to about five minutes at room temperature. After the solvent is removed, the residue can be purified by reversed-phase HPLC.

The 2,4,5-trichlorophenyl esters of the corresponding acids can be prepared conveniently by treating the desired acid with 2,4,5-trichlorophenol in the presence of a coupling agent, such as N,N'-dicyclohexylcarbodiimide. Other methods suitable for preparing acid esters will be apparent to those skilled in the art.

The alkanoic and alkenoic acids used as starting materials for the Abbott, Debono and Fukuda derivatives of formula 4 and the activated derivatives thereof (in particular, the acid chlorides and the 2,4,5-trichlorophenyl esters), are known compounds or can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide. The 2,4,5-trichlorophenyl ester derivative can be purified by column chromatography over silica gel.

The N-alkanoylamino acids or N-alkenoylamino acids used as starting materials for the Debono Group I derivatives of formula 5 are either known compounds or they can be made by acylating the appropriate amino acid with the desired alkanoyl or alkenoyl group using conventional methods. A preferred way of preparing the N-alkanoylamino acids is by treating the appropriate amino acid with an alkanoic acid chloride in pyridine. The alkanoic or alkenoic acids, the activated derivatives thereof, and the amino acids used are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent used to attach the N-alkanoyl or N-alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids used in the synthesis of these products may exist in optically active forms. Both the natural configuration (L-configuration) and unnatural configuration (D-configuration) may be used as starting materials.

The substituted benzoic acids used as starting materials for the Debono II derivatives and the activated derivatives thereof are either known compounds or they can be made from known compounds by methods known in the art. The alkoxybenzoic acids can be prepared conveniently from an appropriate hydroxybenzoic acid by reacting an appropriate alkyl halide with the disodium salt of the appropriate hydroxybenzoic acid.

The hydroxybenzoic acids and substituted derivatives thereof used as starting materials in the processes described herein are either known compounds or can be prepared by conventional methods which are known in the art.

Utility of the Derivatives

The derivatives prepared from the intermediates of this invention, i.e. the compounds of formulas 4 and 5, inhibit the growth of pathogenic bacteria as evidenced by standard biological test procedures. The compounds are useful, therefore, for controlling the growth of bacteria on environmental surfaces (as an antiseptic) or in treating infections caused by bacteria. The antibacterial activity of the compounds has been demonstrated in vitro in agar-plate disc-diffusion tests and in agar-dilution tests and in vivo in tests in mice infected with *Staphylococcus aureus* and *Streptococcus pyogenes*. The compounds are particularly useful in treating infections caused by gram-positive organisms.

When an A-21978C cyclic peptide of this invention is used as an antibacterial agent, it may be administered either orally or parenterally. As will be appreciated by those skilled in the art, the A-21978C compound is commonly administered together with a pharmaceutically acceptable carrier or diluent. The dosage of A-21978C compound will depend upon a variety of considerations, such as, for example, the nature and severity of the particular infection to be treated. Those skilled in the art will recognize that appropriate dosage ranges and/or dosage units for administration may be determined by considering the MIC and ED$_{50}$ values and toxicity data herein provided together with factors such as pharmacokinetics, the patient or host and the infecting microorganism.

EXAMPLE 1

Preparation of A-21978C Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Pre-cooked oatmeal | 60.0 g |
| Yeast | 2.5 g |
| K$_2$HPO$_4$ | 1.0 g |
| Czapek's mineral stock* | 5.0 ml |
| Agar | 25.0 g |
| Deionized water q.s. to | 1 liter |
| pH before autoclaving is about 5.9; adjust to pH 7.2 by addition of NaOH; after autoclaving, pH is about 6.7. | |

*Czapek's mineral stock has the following composition:

| Ingredient | Amount |
|---|---|
| FeSO$_4$.7H$_2$O (dissolved in 2 ml conc HCl) | 2 g |
| KCl | 100 g |
| MgSO$_4$.7H$_2$O | 100 g |
| Deionized water q.s. to | 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| MgSO$_4$.7H$_2$O | 0.25 g |
| CaCO$_3$ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Pre-cooked oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water q.s. to | 1 liter |
| adjust to pH 7.4 with NaOH; after autoclaving, pH is about 6.8. | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen", *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (80 ml), prepared as above-described, is used to inoculate 10 liters of sterile production medium selected from one of the following:

MEDIUM I

| Ingredient | Amount (g/L) |
| --- | --- |
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4.7H_2O$ | 0.25 |
| Tap water | q.s. to 1 liter |

The pH of the medium is about 6.9 after sterilization by autoclaving at 121° C. for 45 minutes at about 16–18 psi.

MEDIUM II

| Ingredient | Amount (g/L) |
| --- | --- |
| Sucrose | 30.0 |
| Peptone | 5.0 |
| $K_2HPO_4$ | 1.0 |
| KCl | 0.5 |
| $MgSO_4.7H_2O$ | 0.5 |
| $FeSO_4.7H_2O$ | 0.002 |
| Deionized water | q.s. to 1 liter |

Adjust to pH 7.0 with HCl; after autoclaving, pH is about 7.0.

MEDIUM III

| Ingredient | Amount (g/L) |
| --- | --- |
| Glucose | 20.0 |
| $NH_4Cl$ | 3.0 |
| $Na_2SO_4$ | 2.0 |
| $ZnCl_2$ | 0.019 |
| $MgCl_2.6H_2O$ | 0.304 |
| $FeCl_3.6H_2O$ | 0.062 |
| $MnCl_2.4H_2O$ | 0.035 |
| $CuCl_2.2H_2O$ | 0.005 |
| $CaCO_3$ | 6.0 |
| $KH_2PO_4$* | 0.67 |
| Tap water | q.s. to 1 liter |

*Sterilized separately and added aseptically. Final pH about 6.6.

The inoculated production medium is allowed to ferment in a 14-liter fermentation vessel at a temperature of about 30° C. for about 66 hours. The fermentation medium is stirred with conventional agitators at about 600 RPM and aerated with sterile air to maintain the dissolved oxygen level above 30% of air saturation at atmospheric pressure.

B. Deacylation of A-21978C

A fermentation of *A. utahensis* is carried out as described in Section A, using slant medium A and production medium I and incubating the production medium for about 67 hours. Crude A-21978C complex (100 g) is added to the fermentation medium.

Deacylation of the A-21978C complex is monitored by assay against *Micrococcus luteus*. The fermentation is allowed to continue until deacylation is complete as indicated by disappearance of activity vs. *M. luteus*, a period of about 24 hours.

C. Isolation of A-21978C Nucleus

Whole fermentation broth (20 liters), obtained as described in Section B, was filtered with a filter aid (Hyflo Super-Cel, Johns Manville Corp.). The mycelial cake was discarded. The filtrate thus obtained was passed through a column containing 1.5 liters of HP-20 resin (DIAION High Porous Polymer, HP-Series, Mitsubishi Chemical Industries Limited, Tokyo, Japan). The effluent thus obtained was discarded. The column was then washed with deionized water (10 L.) to remove residual filtered broth. This wash water was discarded. The column was then eluted with water-:acetonitrile mixtures (10 L. each of 95:5, 9:1, and 4:1), collecting 1-liter fractions.

Elution was monitored by analytical HPLC, using silica gel/$C_{18}$ and a solvent system of water: methanol (3:1) containing 0.1% ammonium acetate, detecting the nucleus with a UV monitor at 254 nm. Fractions containing the nucleus were combined, concentrated under vacuum to remove the acetonitrile and freeze-dried to give 40.6 g of semi-purified A-21978C nucleus.

D. Purification of A-21978C Nucleus

Semi-purified A-21978C nucleus (15 g), obtained as described in Section C, was dissolved in 75 ml of water:-methanol:acetonitrile (82:10:8) containing 0.2% acetic acid and 0.8% pyridine. This solution was pumped onto a 4.7-×192-cm column containing 3.33 L. of silica gel (Quantum LP-1)/$C_{18}$. The column was developed with the same solvent system. Fractions having a volume of 350 ml were collected. Separation was monitored at 280 nm with a UV monitor. Fractions containing the nucleus were combined, concentrated under vacuum to remove solvents and freeze-dried to give 5.2 g of purified A-21978C nucleus.

EXAMPLE 2

Alternate Preparation of A-21978C Nucleus

A-21978C nucleus was prepared according to the method of Example 1 except for certain changes in Section B. The *A. utahensis* culture was incubated initially for about 48 hours; the substrate was semi-purified A-21978C complex (50 g); and incubation after addition of the substrate was about 16 hours. The broth filtrate was passed over a column containing 3.1 liters of HP-20 resin. The column was washed with 10 volumes of water and then was eluted with water:acetonitrile (95:5). Elution was monitored as in Example 1. After collecting 24 liters, the eluting solvent was changed to water:acetonitrile (9:1). Fractions containing the nucleus were eluted with this solvent. These fractions were combined, concentrated under vacuum to remove acetonitrile, and freeze-dried to give 24.3 g of semi-purified A-21978C nucleus.

This semi-purified A-21978C nucleus (24.3 g) was dissolved in water (400 ml). The solution was pumped onto a 4.7-×192-cm steel column containing 3.33 liters of silica gel (Quantum LP-1)/$C_{18}$ prepared in water:methanol:acetonitrile (8:1:1) containing 0.2% acetic acid and 0.8% pyridine. The column was developed with the same solvent at a pressure of about 2000 psi, collecting 350 ml fractions. Elution was monitored by UV at 280 nm. Fractions containing the nucleus were combined, concentrated under vacuum to remove solvents, and freeze-dried to give 14 g of highly purified A-21978C nucleus.

EXAMPLE 3

Preparation of $N_{Orn}$-t-BOC A-21978C Factors $C_2$ and $C_3$

A mixture of A-21978C factors $C_2$ and $C_3$ (10 g), prepared as described in U.S. Pat. No. 4,208,403, was dissolved in water (50 ml) with sonication (200 mg/ml). The pH of the solution was adjusted from 4.05 to 9.5 with 5N NaOH (3.6 ml). Di-tert-butyl dicarbonate (3.0 ml) was added, and the reaction mixture was stirred at room temperature for 2 hours. The pH of the reaction was maintained at 9.5 by manual addition of 5N NaOH (6.5 ml added in 2 hours).

The reaction was monitored periodically by TLC on silica gel, using $CH_3CN:H_2O$ (7:3 and 8:2) solvent systems and detecting by UV.

After about 10 minutes the reaction solution became rapidly turbid, and base consumption increased. After 30 minutes, the rate of increase in turbidity and the rate of base consumption decreased, indicating that the reaction was complete. Nevertheless, the reaction was continued for an additional 90 minutes to insure completion. At the end of the two-hour reaction, the reaction material was lyophilized immediately to give 12.7 g of $N_{Orn}$-t-BOC-A-21978 factors $C_2$ and $C_3$.

Using similar procedures, two 10-g reactions and a 30-g reaction were run. In each of these the reaction time was only 40 minutes. The two 10-g experiments gave 11.9 and 12.1 g of product, respectively. The 30-g reaction gave 35.4 g of product.

EXAMPLE 4

Preparation of A-21978C $N_{Orn}$-t-BOC Nucleus

A. Fermentation of *A. utahensis*

A fermentation of *A. utahensis* was carried out as described in Example 1, Section A, using slant medium A and production medium I and incubating the production medium for about 66 hours.

B. Deacylation of $N_{Orn}$-t-BOC Complex

The A-21978C $N_{Orn}$-t-BOC complex (1185 g of crude substrate which contained about 176 g of A-21978C complex) was added to the fermentation medium. Deacylation was carried out as described in Example 1, Section B. Deacylation was complete, as indicated by HPLC, after about 24 hours.

C. Isolation of A-21978C $N_{Orn}$-t-BOC Nucleus

Fermentation broth (100 L.), obtained as described in Section B, was filtered with a filter aid (Hyflo Supercel). The filtrate was passed over a column containing 7.5 L. of HP-20 resin (DIAION); the column was washed with water (38 L.). Elution was monitored by silica gel/$C_{18}$ HPLC with UV detection at 254 nm. Some nucleus was eluted in the wash. Subsequent elution of nucleus was carried out with water:acetonitrile mixtures as follows: (95:5)-40 L.; (9:1)-40 L.; and (85:15)-100 L. Fractions containing the nucleus were combined, concentrated under vacuum to remove solvent, and freeze-dried to give 298.5 g of semi-purified A-21978C $N_{Orn}$-t-BOC nucleus.

D. Purification of A-21978C $N_{Orn}$-t-BOC Nucleus

Semi-purified A-21978C $N_{Orn}$-t-BOC nucleus (30 g), obtained as described in Section C, was dissolved in water:acetonitrile (9:1) containing 0.2% acetic acid and 0.8% pyridine (75 ml). This solution was applied to a 4.7×192-cm steel column containing 3.33 L. of silica gel (Quantum LP-1)/$C_{18}$ equilibrated in the same solvent system. The column was developed under pressure with water:acetonitrile:methanol (80:15:5) containing 0.2% acetic acid and 0.8% pyridine, collecting 350-ml fractions and detecting product by UV at 280 nm. Fractions containing the product were combined, concentrated under vacuum to remove solvent and freeze-dried to give 18.4 g of purified A-21978C $N_{Orn}$-t-BOC nucleus.

EXAMPLE 5

Alternative Purification of A-21978C $N_{Orn}$-t-BOC Nucleus

Semi-purified A-21978C $N_{Orn}$-t-BOC nucleus (10.8 g), obtained as described in Example 4, Section C, was dissolved in water and applied to a column containing 80 ml of Amberlite IRA-68 (acetate cycle). The column was washed with water and, at a flow rate of 5 ml/min, was eluted sequentially with 0.05N acetic acid (1080 ml), 0.1N acetic acid (840 ml), and 0.2N acetic acid (3120 ml), collecting 120-ml fractions. The column was monitored with analytical HPLC over silica gel/$C_{18}$, using a system of water:acetonitrile:methanol (80:15:5) containing 0.2% ammonium acetate and detecting product with UV at 254 nm. Fractions containing the product were combined; the pH of the solution was adjusted to 5.8 with pyridine; the resulting solution was concentrated under vacuum to a volume of about 200 ml. Water was added to the concentrate, and the resulting solution was reconcentrated to remove pyridine. This concentrate was freeze-dried to give 3.46 g of purified A-21978C $N_{Orn}$-t-BOC nucleus.

EXAMPLE 6

Preparation of an Abbott, Debono and Fukuda Derivative

The following procedure illustrates the preparation of the compounds of formula 4 by the "active ester" method. The specific compounds prepared by this procedure are the compounds of formula 4 wherein R is $CH_3(CH_2)_8CO$— (n-decanoyl), $R^1$, $R^3$, $R^4$ and $R^5$ are hydrogen and $R^2$ is t-BOC or hydrogen.

$N_{Trp}$-(n-Decanoyl) A-21978C Nucleus

A. Preparation of 2,4,5-Trichlorophenyl n-Decanoate

A solution of decanoyl chloride (Pfaltz and Bauer, 5.6 ml) and 2,4,5-trichlorophenol (5.6 g) in diethyl ether (1 L) and pyridine (120 ml) is stirred for 4 hours. The reaction mixture is filtered and dried in vacuo. The 2,4,5-trichlorophenyl n-decanoate is purified on a silica-gel column (Woelm), using toluene as the eluent. Fractions are monitored by TLC, using short-wave UV for detection. Appropriate fractions are pooled and dried in vacuo to give 10.4 g of 2,4,5-trichlorophenyl n-decanoate.

B. Acylation of $N_{Orn}$-t-BOC-A-21978C Nucleus with 2,4,5-Trichlorophenyl n-Decanoate A solution of $N_{Orn}$-t-BOC A-21978C nucleus (15.0 g) and 2,4,5-trichlorophenyl n-decanoate (15.0 g) in dry DMF (500 ml) is stirred under $N_2$ at ambient temperature for 25 hours. The mixture is then stirred at 60° C. for 5 hours or until TLC shows reaction completion. The reaction mixture is concentrated in vacuo to about 200 ml and is stirred with 1.2 liters of $Et_2O$/toluene (5:1). The product is separated by filtration, washed with $Et_2O$, and dried under vacuum to give 15.05 g of the $N_{Trp}$-(n-decanoyl)-$N_{Orn}$-t-BOC A-21978C nucleus intermediate (formula 4: R=n-decanoyl, $R^1$, $R^3$, $R^4$, $R^5$=H, $R^2$=t-BOC).

C. Purification of $N_{Trp}$-(n-Decanoyl)-$N_{Orn}$-t-BOC-A-21978C Nucleus

The $N_{Trp}$-(n-decanoyl)-$N_{Orn}$-t-BOC-A-21978C nucleus intermediate is purified in the following manner: The crude preparation is dissolved in about 50 ml of the eluting solvent system, and this is purified by HPLC, using the Waters Prep 500 system containing a cartridge packed with reversed-phase $C_{18}$ silica-gel adsorbent. The system is eluted with $H_2O$:MeOH:-$CH_3CN$(50:15:35) containing 0.2% pyridine and 0.2% HOAc. Fractions are monitored by UV at 280 nm. Appropriate fractions are combined and dried in vacuo to give 8 56 g of purified $N_{Trp}$-(n-decanoyl)-$N_{Orn}$-t-BOC-A-21978C nucleus.

D. Removal of the $N_{Orn}$-t-BOC Group

The t-BOC group is removed by stirring $N_{Trp}$-(n-decanoyl)-$N_{Orn}$-t-BOC A-21978C nucleus (1.47 g) in 15 ml of trifluoroacetic acid/1,2-ethanedithiol (10:1) at ambient temperature for 3 minutes. The reaction mixture is dried in vacuo, and the residue is triturated with $Et_2O$ (50 ml). After a 20-ml $Et_2O$ wash, the triturate is dried in vacuo to give 2.59 g of crude $N_{Trp}$-(n-decanoyl)-A-21978C nucleus (formula 4: R=n-decanoyl; $R^1$, $R^2$, $R^3$, $R^4$, $R^5$=H).

E. Purification of $N_{Trp}$-(n-Decanoyl)-A-21978C Nucleus

The crude $N_{Trp}$-(n-decanoyl)-A-21978C nucleus is purified by reversed-phase HPLC in the following manner: The sample (2.59 g), dissolved in 4.0 ml of $H_2O$:-MeOH:$CH_3CN$:pyridine:HOAc (50:15:35:2:2), is injected into a 33-×1-inch stainless-steel column packed with LP-1/$C_{18}$ adsorbent. The column is eluted with this same solvent system. Elution is performed at a pressure of 1200–1700 psi with a flow rate of 10–12 ml/min, using an LDC duplex pump (Milton-Roy). The effluent is monitored by a UV detector (Isco Model UA-5, Instrument Specialist Co., 4700 Superior Avenue, Lincoln, Nebr. 68504) at 280 nm. Fractions (20–24 ml) are collected every two minutes. The desired fractions, as indicated by antimicrobial activity, are combined and dried in vacuo to give 1.05 g of product.

This purification procedure was repeated with 4.35 g, 4.25 g, 2.14 g, 2.00 g and 1.75 g crude starting derivative to give a total of 5.58 g of purified $N_{Trp}$-(n-decanoyl)-A-21978C nucleus.

EXAMPLE 7

Preparation of a Debono Group I Derivative

This example illustrates the preparation of the Debono Group I compounds of formula 5. The specific compounds prepared by this procedure are the compounds of formula 5 wherein R is N-(n-decanoyl)-L-phenylalanyl and $R^2$ is t-BOC or hydrogen.

Preparation of $N_{Trp}$-[N-(n-Decanoyl)-L-phenylalanyl]-A-21978C Nucleus

A. Preparation of N-(n-Decanoyl)-L-phenylalanyl 2,4,5-Trichlorophenolate

A solution of N-(n-decanoyl)-L-phenylalanine (31.9 g, 0.1 mole) and 2,4,5-trichlorophenol (19.7 g, 0.1 mole) in 1 liter of anhydrous ether was treated with N,N'-dicyclohexylcarbodiimide (20.6 g, 0.1 mole). The reaction was stirred overnight at room temperature. The precipitated N,N'-dicyclohexylurea was removed by filtration and discarded. The filtrate was concentrated under vacuum to dryness. The residue obtained was triturated with ether, and the solids (residual cyclohexylurea) were removed by filtration. The filtrate was evaporated to dryness under reduced pressure. The residue was crystallized from acetonitrile to give 36.9 g of crystalline N-(n-decanoyl)-L-phenylalanyl 2,4,5-trichlorophenolate, m.p. 122°–124° C.

B. Preparation of $N_{Trp}$-[N-(n-Decanoyl)-L-phenylalanyl]-$N_{Orn}$-t-BOC-A-21978C Nucleus A solution of N-(n-decanoyl)-L-phenylalanyl 2,4,5-trichlorophenolate (10 g, 0.02 mole), $N_{Orn}$-t-BOC-A-21978C nucleus (10 g, 0.006 mole) in anhydrous DMF (1 L) was stirred at room temperature for 96 hours under an atmosphere of nitrogen. The solvent was removed by evaporation under reduced pressure. The residual material was stirred with a mixture of diethyl ether (800 ml) and chloroform (200 ml) for 2 hours. The product was separated by filtration to give a light brown powder (10.3 g). This material (9.9 g) was dissolved in methanol (200 ml) and purified by preparative HPLC, using a "Prep LC/System 500" unit and a Prep-Pak-500/$C_{18}$ Column as the stationary phase. The column was eluted isocratically, using a water:methanol:acetonitrile (2:1:2) solvent system and collecting 250-ml fractions at a rate of one fraction per minute. The desired compound was eluted in the 9th through the 22nd fractions.

Fractions were combined on the basis of TLC [reversed phase silica gel/$C_{18}$; developed with water:methanol:acetonitrile (3:3:4); detected with Van Urk spray]. Combined fractions were examined by bioautography [silica gel TLC acetonitrile:acetone:water (2:2:1) solvent system and *Micrococcus luteus* as the detecting organism] and were shown to consist of a single bioactive component. This procedure gave 6.02 g of $N_{Trp}$-[N-(n-decanoyl)-L-phenylalanyl]-$N_{Orn}$-t-BOC-A-21978C nucleus [compound of formula 5: R=N-(n-decanoyl-L-phenylalanyl); $R^1$=t-BOC].

C. Preparation of $N_{Trp}$-[N-(n-Decanoyl)-L-phenylalanyl]-A-21978C Nucleus A flask (100 ml) was cooled to 5° C. in an icebath. $N_{Trp}$-[N-(n-decanoyl)-L-phenylalanyl]-$N_{Orn}$-t-BOC A-

21978C nucleus (6.02 g, 0.008 mole), prepared as described in Section B, and then anhydrous trifluoroacetic acid containing 2% anisole (50 ml) were added to the flask. The mixture, which went into solution in approximately two minutes, was stirred under an atmosphere of nitrogen for ten minutes. The solution was evaporated to dryness under reduced pressure at below 40° C. to give a gummy solid which was triturated twice with a diethyl ether:dichloromethane (4:1) solution (two 100-ml volumes). The solids were collected by filtration and washed with diethyl ether to give the TFA salt. This was dissolved in water (50 ml), and the pH of the solution was adjusted to 5.4 with pyridine. The solution was then lyophilized to give 6.1 g of off-white lyophilizate.

The lyophilizate, dissolved in methanol (35 ml), was purified using a reverse-phase $C_{18}$ silica-gel column (Waters Associates, Prep 500), eluting in stepwise gradient with $H_2O:CH_3OH:CH_3CN$ containing 0.1% pyridinium acetate at ratios of 3:1:2, 2:1:2 and 1:2:2 and collecting fractions having a volume of 250 ml. The desired product was eluted during the 2:1:2 elution. The fractions containing the product were lyophilized to give 2.23 g of creme-colored $N_{Trp}$-[N-(n-decanoyl)-L-phenylalanyl]-A-21978C nucleus (compound of formula 5: R=N-(n-decanoyl)-L-phenylalanyl; $R^1$=H).

The product was evaluated by analytical HPLC [reversed-phase $C_{18}$ silica-gel column, MeOH:$CH_3CN$:$H_2O$:PyOAc (15:35:49:1) solvent and UV detection at 230 nm], by TLC [reversed-phase $C_{18}$ silica-gel plates (Whatman), $H_2O:CH_3OH:CH_3CN$ (3:3:4) solvent and Van Urk's spray and short-wave UV for detection] and by bioautography [silica-gel TLC (Merck), an $H_2O:CH_3CN$:acetone (1:2:2) solvent, and *Micrococcus luteus* as the detecting organism]. Each of these methods demonstrated that the product was homogenous. Substitution at the tryptophan N-terminus position was confirmed by 360 MHz PMR. Amino-acid analysis confirmed the incorporation of one equivalent of L-phenylalanine into the product.

EXAMPLE 8

Preparation of a Debono Group II Derivative

The following procedure illustrates the preparation of the Debono Group II compounds of formula 5. The specific compounds prepared by this procedure are the compounds of formula 5 wherein R is p-(n-dodecyloxy)benzoyl and $R^1$ is t-BOC or hydrogen.

A. Preparation of $N_{Trp}$-p-(n-Dodecyloxy)benzoyl-$N_{Orn}$-t-BOC-A-21978C Nucleus A solution of p-(n-dodecyloxy)benzoyl 2,4,5-trichlorophenolate (0.9 g, mole), A-21978C t-BOC nucleus (0.9 gm, mole) in 400 ml of anhydrous dimethylformamide was allowed to stir at room temperature for 120 hours under an atmosphere of nitrogen. The solvent was removed by evaporation under reduced pressure. The residual material was stirred with a mixture of diethyl ether (400 ml) and chloroform (400 ml) for 2 hours. The product was separated by filtration and dried to give a light brown powder (0.962 g). A portion of this material (0.78 g) was dissolved in methanol (200 ml) and purified by preparative HPLC, using a "Prep LC/ System 500" unit (Waters Associates, Inc., Milford Mass.) and a Prep Pak-500/$C_{18}$ Column (Waters Associates) as a stationary phase. The column was operated isocratically, using a water:methanol:acetonitrile (2:1:2) solvent system and collecting 250-ml fractions (1 fraction/min.). The desired compound was eluted in the 2nd to the 6th fractions.

Fractions were combined on the basis of TLC [reverse phase/$C_{18}$ silica gel, developed with water:methanol:acetonitrile (3:3:4), detected with Van Urk spray]. Bioautography of the combined fractions, using silica gel TLC, an acetonitrile:acetone:water (2:2:1) solvent, and *Staphylococcus aureus* as the detecting organism, indicated that the product was a single bioactive component. This procedure gave 0.421 g of $N_{Trp}$-p-(n-dodecyloxy)benzoyl-$N_{Orn}$-t-BOC-A-21978C nucleus.

B. Preparation of $N_{Trp}$-p-(n-dodecyloxy)benzoyl-A-21978C Nucleus $N_{Trp}$-p-(n-Dodecyloxy)benzoyl-$N_{Orn}$-t-BOC-A-21978C nucleus (230 mg) was dissolved in 5 ml of trifluoroacetic acid containing 2% anisole and stirred for 5 minutes at 0° C. The solution was concentrated to an oil under vacuum, and the oil was triturated with $Et_2O$ (100 ml). The solids were separated, air-dried, and taken up in water (10 ml). The pH of this solution was adjusted from 3.25 to 7 by the addition of pyridine. The resulting solution was lyophilized to give 179 mg of white amorphous $N_{Trp}$-p-(n-dodecyloxy)benzoyl-A-21978C nucleus. This compound has an $R_f$ value of about 0.78 on silica-gel TLC, using an acetonitrile:acetone:water (2:2:1) solvent system and Van Urk spray for detection.

EXAMPLE 9

The antibacterial activity of the compounds of formulas 4 and 5 can be demonstrated in vitro in standard agar-plate disc-diffusion tests and agar-dilution tests and in vivo in standard tests in mice which assess effectiveness against a systemic bacterial infection. The results of the antibacterial testing of representative compounds of formulas 4 and 5 are set forth in Tables I, II, and III.

Table I gives the results of the testing in vitro of the compounds of Examples 6–8 by agar-plate disc-diffusion methods. In the tests summarized in Table I the compounds did not show activity against the following organisms at the levels tested: *Saccharomyces cerevisiae* ATCC 2366, *Neurospora crassa*, *Candida albicans*, *Trichophyton mentagrophytes*, *Proteus vulgaris* ATCC 9484, *Salmonella gallinarum*, *Escherichia coli* ATCC 4157, *Pseudomonas aeruginosa* ATCC 9027, *Serratia marcescens* NRRL B284, or *Pseudomonas solanacearun*.

Table II gives the results of the testing of the compounds of Examples 6–8 by standard agar-dilution tests. In Table II activity is measured by the minimal inhibitory concentration (MIC), i.e. the lowest concentration at which the test compound inhibits growth of the microorganism. In the tests summarized in Table II the compounds were not active against strains of the following organisms at the levels tested: *Haemophilus influenzae*, *Shigella sonnei*, *Escherichia coli*, *Klebsiella pneumoniae*, *Enterobacter aerogenes*, *Enterobacter cloacae*, *Salmonella typhi*, *Pseudomonas aeruginosa*, *Serratia marcescens*, *Proteus morganii*, *Proteus inconstans*, *Proteus rettgeri*, *Citrobacter freundii* and *Bordetella bronchiseptica*.

The results of in vivo tests to evaluate the effectiveness of the derivatives against experimental bacterial infections in mice are given in Table III. In these tests two doses of test compound were administered subcutaneously or orally to mice with illustrative infections.

The activity observed was measured as an ED$_{50}$ value [effective dose in mg/kg to protect fifty percent of the test animals: See Warren Wick, et al., *J. Bacteriol.* 81, 233-235 (1961)].

The toxicity of representative compounds of formulas 4 and 5 is set forth in Table IV.

TABLE I

Antibacterial Activity of Formula 1 Compounds by the Agar-Plate Disc-Diffusion Test

| Compound | | | Size of Zone of Inhibition (mm)$^a$ | | | |
|---|---|---|---|---|---|---|
| Example No. | Formula No. | $N_{Trp}$ Substituent | *Staphylococcus aureus* ATCC 6738P | *Bacillus subtilis* ATCC 6633 | *Micrococcus luteus* ATCC 9341 | *B. subtilis* ATCC 6633$^b$ |
| 6 | 4 | CH$_3$(CH$_2$)$_8$CO— | 24 | 20 | 22 | 29 |
| 7 | 5 | (L)CH$_3$(CH$_2$)$_8$CONHCH(CH$_2$C$_6$H$_5$)CO— | 30 | 22 | 24 | 31 |
| 8 | 5 |  CH$_3$(CH$_2$)$_{11}$O—⟨ ⟩—CO— | 20 | 13 | 18 | 20 |

$^a$Compounds were suspended in water at a concentration of 1 mg/ml; a 7-mm disc was dipped into the suspension and then placed on the agar surface; incubation: 24–48 hours at 25–37° C.
$^b$Grown on minimal nutrient agar

TABLE II

Antibacterial Activity by the Agar-Dilution Test

| | MIC Values of Test Compounds$^a$ | | |
|---|---|---|---|
| Test Organism | 6$^d$ | 7$^e$ | 8 |
| *Staphylococcus aureus* X1.1 | 1, 0.5 | 0.5 | 1 |
| *Staphylococcus aureus* V41$^b$ | 1, 0.5 | 0.5 | 1 |
| *Staphylococcus aureus* X400$^c$ | 2, 1 | 1 | 2 |
| *Staphylococcus aureus* S13E | 1, 0.5 | 0.5 | 1 |
| *Staphylococcus epidermidis* EPI1 | 2, 1 | 1 | 4 |
| *Staphylococcus epidermidis* EPI2 | 1, 0.5 | 0.5 | 2 |
| *Streptococcus pyogenes* C203 | 0.25, 0.125 | 0.25 | 0.25 |
| *Streptococcus pneumoniae* Park I | 1, 0.5 | 0.5 | 0.015 |
| Streptococcus Group D X66 | 16, 16 | 8 | 2 |
| Streptococcus Group 9960 | 2, 2 | 2 | 1 |

$^a$MIC in mcg/ml; compound numbers = example numbers
$^b$Penicillin-resistant strain
$^c$Methicillin-resistant-strain
$^d$Two experiments
$^e$Median value for three experiments

TABLE III

In Vivo Activity Of A-21978C Cyclic Peptides

| Compound | | | ED$_{50}$ Values$^a$ | | |
|---|---|---|---|---|---|
| Example No. | Formula No. | $N_{Trp}$ Substituent | *Staphylococcus aureus* subcutaneous | Streptococcus subcutaneous | pyogenes oral |
| 6 | 4 | CH$_3$(CH$_2$)$_8$CO— | 0.28 | 0.03 | 66 |
| 7 | 5 | (L)CH$_3$(CH$_2$)$_8$CONHCH(CH$_2$C$_6$H$_5$)CO— | 0.7, 0.98$^b$ | 0.39 | >200 |
| 8 | 5 |  CH$_3$(CH$_2$)$_{11}$O—⟨ ⟩—CO— | 3.35 | 0.31 | >200 |

$^a$mg/kg × 2
$^b$Two experiments

TABLE IV

Toxicity of A-21978C Cyclic Peptides

| Compound | | | LD$_{50}$ (mg/kg) in Mice$^a$ |
|---|---|---|---|
| Example No. | Formula No. | $N_{Trp}$ Substituent | |
| 6 | 4 | CH$_3$(CH$_2$)$_8$CO— | >300 |
| 7 | 5 | (L)CH$_3$(CH$_2$)$_8$CONHCH(CH$_2$C$_6$H$_5$)CO— | 600 |
| 8 | 5 | CH$_3$(CH$_2$)$_{11}$O—⟨ ⟩—CO— | 67.5 |

$^a$Administered intravenously

We claim:

1. The method of deacylating an antibiotic selected from the group consisting of A-21978C complex, A-21978C factors C$_0$, C$_1$, C$_2$, C$_3$, C$_4$, and C$_5$, blocked A-21978C complex, and blocked A-21978C factors C$_0$, C$_1$, C$_2$, C$_3$, C$_4$ and C$_5$ which comprises exposing the antibiotic in an aqueous medium to an enzyme which deacylates and which is produced by a microorganism of the family Actinoplanaceae until substantial deacylation is accomplished.

2. The method of claim 1 wherein the microorganism of the family Actinoplanaceae is a member of the genus Actinoplanes.

3. The method of claim 2 wherein the microorganism is *Actinoplanes utahensis*.

4. The method of claim 3 wherein the microorganism is *A. utahensis* NRRL 12052 or a mutant thereof which produces the enzyme.

5. The method of claim 4 wherein the microorganism is *A. utahensis* NRRL 12052.

6. The method of claim 1 wherein the microorganism is *Streptosporangium roseum* var. *hollandensis* NRRL 12064, or a mutant thereof which produces the enzyme.

7. The method of claim 6 wherein the microorganism is *Streptosporangium roseum* var. *hollandensis* NRRL 12064.

8. The method of claim 2 wherein the microorganism is *Actinoplanes missouriensis* NRRL 12053 or a mutant thereof which produces the enzyme.

9. The method of claim 8 wherein the microorganism is *Actinoplanes missouriensis* NRRL 12053.

10. The method of claim 2 wherein the microorganism is Actinoplanes sp. NRRL 12065 or a mutant thereof which produces the enzyme.

11. The method of claim 10 wherein the microorganism is Actinoplanes sp. NRRL 12065.

12. The method of claim 2 wherein the microorganism is Actinoplanes sp. NRRL 8122 or a mutant thereof which produces the enzyme.

13. The method of claim 12 wherein the microorganism is Actinoplanes sp. NRRL 8122.

14. A method of claim 1 wherein the enzyme is present in a culture of the producing Actinoplanaceae microorganism.

15. A method of claim 1 wherein the antibiotic is A-21978C complex.

16. A method of claim 1 wherein the antibiotic is A-21978C factor $C_0$.

17. A method of claim 1 wherein the antibiotic is A-21978C factor $C_1$.

18. A method of claim 1 wherein the antibiotic is A-21978C factor $C_2$.

19. A method of claim 1 wherein the antibiotic is A-21978C factor $C_3$.

20. A method of claim 1 wherein the antibiotic is A-21978C factor $C_4$.

21. A method of claim 1 wherein the antibiotic is A-21978C factor $C_5$.

22. A method of claim 1 wherein the antibiotic is blocked A-21978C complex.

23. A method of claim 1 wherein the antibiotic is selected from blocked A-21978C factors $C_0$, $C_1$, $C_2$, $C_3$, $C_4$ and $C_5$.

* * * * *